US010926987B2

(12) United States Patent
Lizari Illarramendi et al.

(10) Patent No.: US 10,926,987 B2
(45) Date of Patent: Feb. 23, 2021

(54) DEVICE FOR PLACING SCREW CAPS IN CONTAINERS

(71) Applicant: Kiro Grifols, S.L., Arrasate (ES)

(72) Inventors: Borja Lizari Illarramendi, Araico (ES); Amaia Ilzarbe Andres, Donostia-San Sebastian (ES); Jose Ignacio Andres Pineda, Vitoria-Gasteiz (ES); Clara Molinuevo Portal, Burgos (ES)

(73) Assignee: Kiro Grifols, S.L., Arrasate (ES)

(*) Notice: Subject to any disclaimer, the term of this patent is extended or adjusted under 35 U.S.C. 154(b) by 407 days.

(21) Appl. No.: 15/651,394

(22) Filed: Jul. 17, 2017

(65) Prior Publication Data
US 2018/0099847 A1    Apr. 12, 2018

(30) Foreign Application Priority Data

Oct. 10, 2016  (ES) .............................. ES201631309

(51) Int. Cl.
*B67B 3/20*     (2006.01)
*A61M 5/32*    (2006.01)
(Continued)

(52) U.S. Cl.
CPC ......... *B67B 3/2053* (2013.01); *A61M 5/3202* (2013.01); *B65B 3/006* (2013.01);
(Continued)

(58) Field of Classification Search
CPC ....... B67B 3/20; B67B 3/2053; B67B 3/2066; B67B 7/2807
(Continued)

(56) References Cited

U.S. PATENT DOCUMENTS 979,766  A  * 12/1910  Jenkins ..................... B67B 1/10
                                                                  53/305
1,989,039 A  *  1/1935  Geyer ................... B65B 7/2842
                                                                  53/310

(Continued)

FOREIGN PATENT DOCUMENTS

EP       2537764 A1    12/2012
WO    2011/010963 A1    1/2011

OTHER PUBLICATIONS

Search report dated Feb. 28, 2017 in corresponding ES Application No. 201631309.

(Continued)

*Primary Examiner* — Thanh K Truong
*Assistant Examiner* — David G Shutty
(74) *Attorney, Agent, or Firm* — Knobbe, Martens, Olson & Bear, LLP

(57) ABSTRACT

A device for placing threaded lids on containers includes a holder for lids to be placed and a mechanism for retaining the lids stored in the holder. The retaining mechanism has a predetermined retaining position in which the lids stored in the holder are retained and a release position in which one of the lids stored in the holder is dispensed. The device also includes a lid positioner, which places a threaded lid on a container through a first rotation about a first axis when the positioner is in the placing position. When the position is in the receiving position, the positioner causes the retaining mechanism to change from the predetermined retaining position to the release position through rotation about the first axis.

14 Claims, 11 Drawing Sheets

(51) Int. Cl.
  *B65B 7/28* (2006.01)
  *B65B 3/00* (2006.01)

(52) U.S. Cl.
  CPC .......... *B65B 7/2807* (2013.01); *B65B 7/2835* (2013.01); *B67B 3/20* (2013.01); *B67B 3/2066* (2013.01); *B67B 2201/06* (2013.01)

(58) Field of Classification Search
  USPC .................. 53/285, 287, 309, 317, 331.5
  See application file for complete search history.

(56) References Cited

U.S. PATENT DOCUMENTS

| | | | | |
|---|---|---|---|---|
| 3,151,426 A * | 10/1964 | Pechmann | ................ | B67B 1/06 53/297 |
| 3,214,886 A * | 11/1965 | Pechmann | ............ | B67B 3/2033 53/304 |
| 3,309,838 A * | 3/1967 | Wilhere | .................. | B67B 3/206 53/67 |
| 3,975,886 A * | 8/1976 | Waters | ...................... | B67B 3/24 53/310 |
| 4,222,214 A * | 9/1980 | Schultz | ................. | B67B 3/2073 279/33 |
| 4,683,706 A | 8/1987 | Harper | | |
| 5,115,617 A * | 5/1992 | Lewis | ................... | B65B 7/2835 53/306 |
| 5,321,934 A * | 6/1994 | Bech | ........................ | B65B 7/28 53/329.2 |
| 5,400,564 A * | 3/1995 | Humphries | ........... | B65B 7/2835 53/308 |
| 5,746,042 A * | 5/1998 | Lombardi | ............. | B65B 7/2807 53/305 |
| 7,010,902 B2 * | 3/2006 | Pagh | ..................... | B65B 7/2807 53/309 |
| 7,353,643 B2 * | 4/2008 | Cirio | ................. | B65G 47/5104 53/290 |
| 8,955,292 B2 * | 2/2015 | Schraudolph | ......... | B65B 7/2835 53/331.5 |
| 9,487,312 B2 * | 11/2016 | Bianco | ....................... | B65B 3/02 |
| 2011/0083405 A1 * | 4/2011 | Dewert | ................. | B67B 3/2033 53/490 |
| 2011/0162332 A1 * | 7/2011 | Hecktor | .................... | B67B 3/06 53/488 |
| 2016/0023874 A1 * | 1/2016 | Schraudolph | ............. | B67B 3/06 53/490 |

OTHER PUBLICATIONS

Extended European Search Report dated Jan. 4, 2018 for Application No. 17382351.9 in 9 pages.

* cited by examiner

DEVICE FOR PLACING SCREW CAPS IN CONTAINERS

CROSS-REFERENCE TO RELATED APPLICATION

This application claims priority to Spanish Patent Application No. P 201631309 filed on Oct. 10, 2016, the disclosure of which, including the specification, the drawings, and the claims is hereby incorporated by reference in its entirety.

FIELD

The present disclosure relates, at least in part, to a device for placing threaded lids on containers and, in particular, relates to a device for placing lids on syringes intended for containing intravenous medication in liquid form; however the use of said device is not limited to said application.

BACKGROUND

Known devices are considerably complex and require components having multiple degrees of freedom such that threaded lids can be dispensed and placed on containers automatically, which causes various kinds of problems. For example, manufacturing devices of this kind is costly and, as a result, the product is expensive on the market. Furthermore, maintenance of the product by the user is costly as well as tricky. Finally, the energy consumption of said complex devices is high.

SUMMARY

The present invention aims to overcome the aforementioned disadvantages of known devices for placing threaded lids on containers. To that effect, the present invention discloses a device for placing threaded lids on containers, said device comprising:
  a holder for lids to be placed, said holder comprising an exit through which the lids stored in said holder are dispensed,
  a mechanism for retaining the lids stored in said holder, said retaining mechanism being arranged at the exit of said holder, said retaining mechanism having a predetermined retaining position in which the lids stored in said holder are retained, and a release position in which one of the lids stored in said holder is dispensed, and
  a threaded-lid positioner which is designed to move between a receiving position and a placing position, said positioner being able to rotate about a first axis, said positioner placing a threaded lid on a container, by means of a first rotation about said first axis, when said positioner is in said placing position,
characterized in that said positioner, when in said receiving position, causes the retaining mechanism to change from the predetermined retaining position to the release position by means of a rotation about said first axis.

The present invention allows a threaded lid to be dispensed and then placed on a container by means of a single active lid handler. Moreover, said single handler is able to carry out the lid dispensing and placing operations by means of rotations about the same axis, i.e. by means of a single degree of freedom. In this way, the number of degrees of freedom required for operation of the device is minimal.

Furthermore, the positioner can be the only active component of the device. Its function is to dispense the lids by acting on the lid-retaining mechanism and to place the lids on the containers.

In light of the above, the present invention provides a simpler device that is less costly to manufacture and maintain.

Preferably, said rotation about said first axis that causes the retaining mechanism to change from the predetermined retaining position to the release position is a second rotation different from the first rotation.

Optionally, the retaining mechanism can rotate about a second axis parallel to said first axis, said mechanism changing from the predetermined retaining position to the release position by means of rotations about said second axis.

The retaining mechanism can also comprise, for example, resilient means for returning to the predetermined retaining position, starting from the release position.

In one embodiment of a device according to the present invention, the retaining mechanism comprises a first arm and a second arm for supporting lids to be dispensed, said arms being rotatably interconnected. Said first arm can comprise, for example, a rest on which a first lid to be dispensed rests when the retaining mechanism is in the predetermined retaining position.

Furthermore, said second arm can comprise, for example, a projection which comes into contact with a second lid to be dispensed when the retaining mechanism is in the release position.

Preferably, the positioner comprises a rod that is eccentric with respect to said first axis, such that the rotation of the positioner about said first axis defines a trajectory of said rod.

Advantageously, the first arm of the retaining mechanism intercepts said trajectory of said rod of the positioner such that, when the positioner carries out said second rotation about said first axis, said rod comes into contact with said first arm, causing said retaining mechanism to rotate from the predetermined retaining position to the release position.

In this way, the lids are dispensed in an entirely mechanical manner, without additional power sources being required, and in a passive manner by the lid-retaining mechanism.

Optionally, the positioner comprises a region for receiving a lid.

In one embodiment of the device according to the present invention, the lid holder comprises an entrance for manually supplying lids to the holder. In order to prevent the lids from being placed in an incorrect orientation, said entrance can, for example, be sized so as to match the dimensions of the lid, and can have a raised surface supported by a spring.

BRIEF DESCRIPTION OF THE FIGURES

To aid understanding, an embodiment of a device for placing threaded lids on containers, to which the present invention relates, is described below with reference to explanatory yet non-limiting drawings of the present invention.

DETAILED DESCRIPTION

Figure 1:
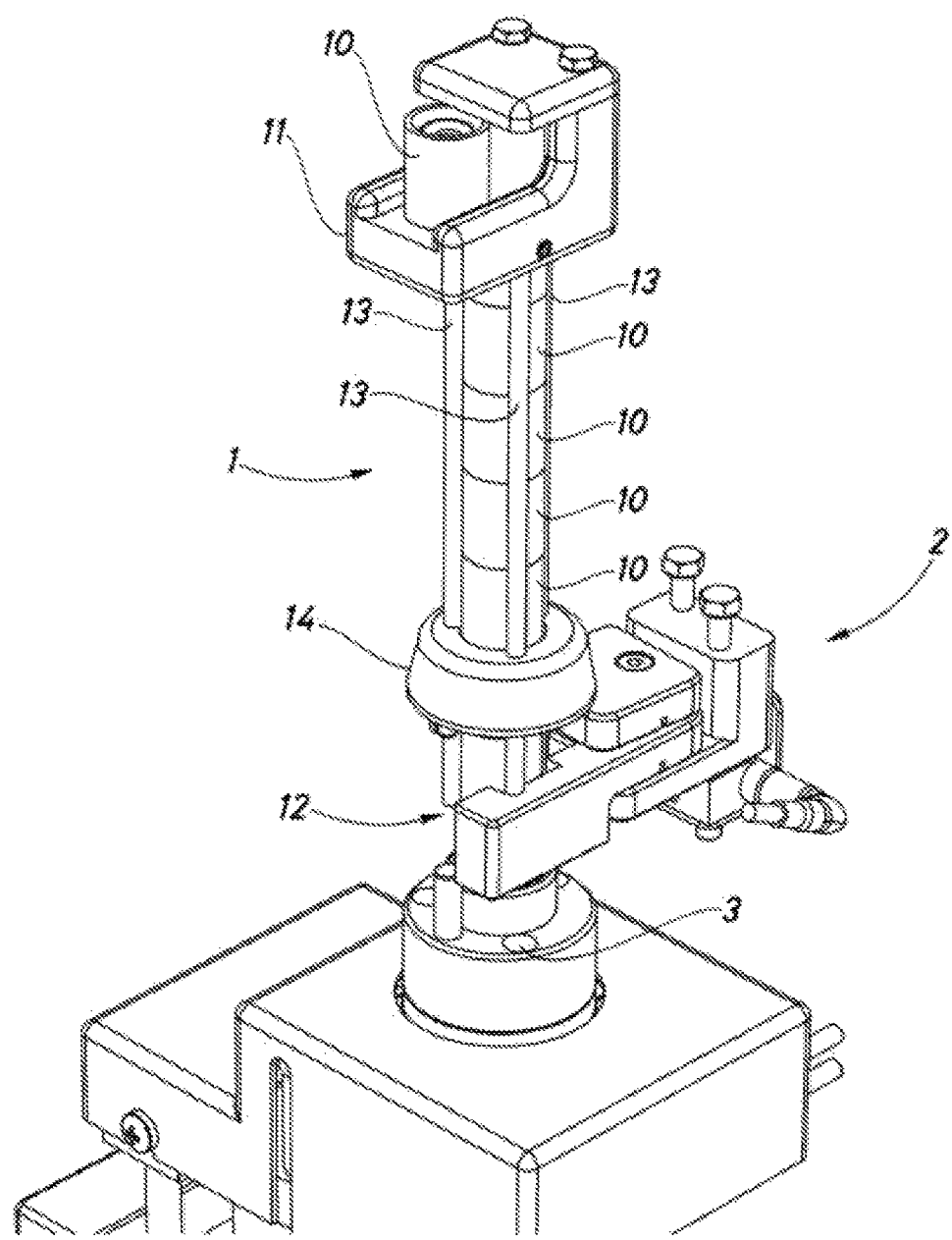
FIG. 1 is a perspective view showing an embodiment of a lid-placing device according to the present invention.

In the embodiment from FIG. 1, a device for placing threaded lids on containers is shown. Specifically, this is an example of a device for placing threaded lids on syringes having a Luer-Lock connection.

The device comprises a holder -1- for lids to be placed, in which threaded lids -10- are stored one on top of the other and introduced through an entrance opening -11- of the holder -1-. A retaining mechanism -2- for the lids -10- in the holder is arranged at the exit -12- of the holder, the function of which retaining mechanism is to retain and dispense the lids -10-. The lids -10- dispensed by the retaining mechanism -2- are placed on the lid positioner -3-.

The holder -1- comprises three columns -13- (see FIG. 1) arranged so as to be equidistant from one another. The columns -13- of the holder are supported by a base -14- that is attached to a fixed platform (not shown for reasons of clarity). The three columns -13- support the entrance opening -11- of the holder -1-.

Figure 2:
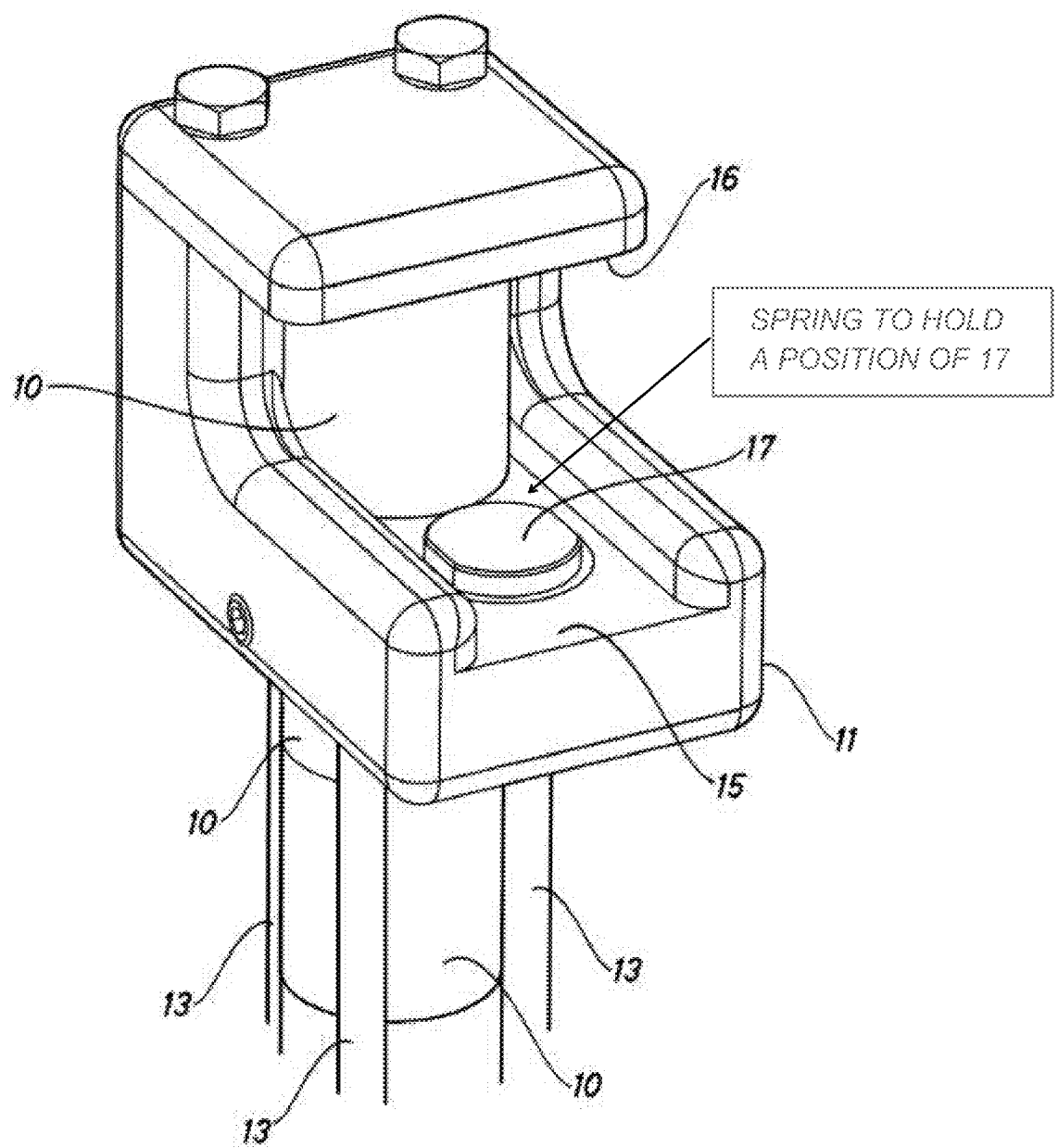
FIG. 2 is a perspective view of a detail of the manual lid entrance of the device from FIG. 1.

As shown in FIG. 2, the entrance opening -11- of the holder -1- has a surface -15- for receiving lids -10- that comprises a stop -16- and a projection -17- that is held in the position thereof by the action of a spring (not shown). The entrance opening -11- prevents the lids -10- from being placed upside down in the holder -1-. For this purpose, the stop -16- forces the lids -10- to be placed on top of the projection -17- before being introduced into the holder -1-, such that the only way to introduce a lid -10- into the holder -1- is to press said projection -17- against the force exerted by the spring that supports it such that it is flush with the receiving surface -15-. Given that lids -10- for Luer-Lock connections have a face having a hollow interior and a solid face, there is only one orientation in which the lid can be introduced into the holder -1-, i.e. placing the solid face of the lid -10- on top of the projection -17-.

Figure 3:
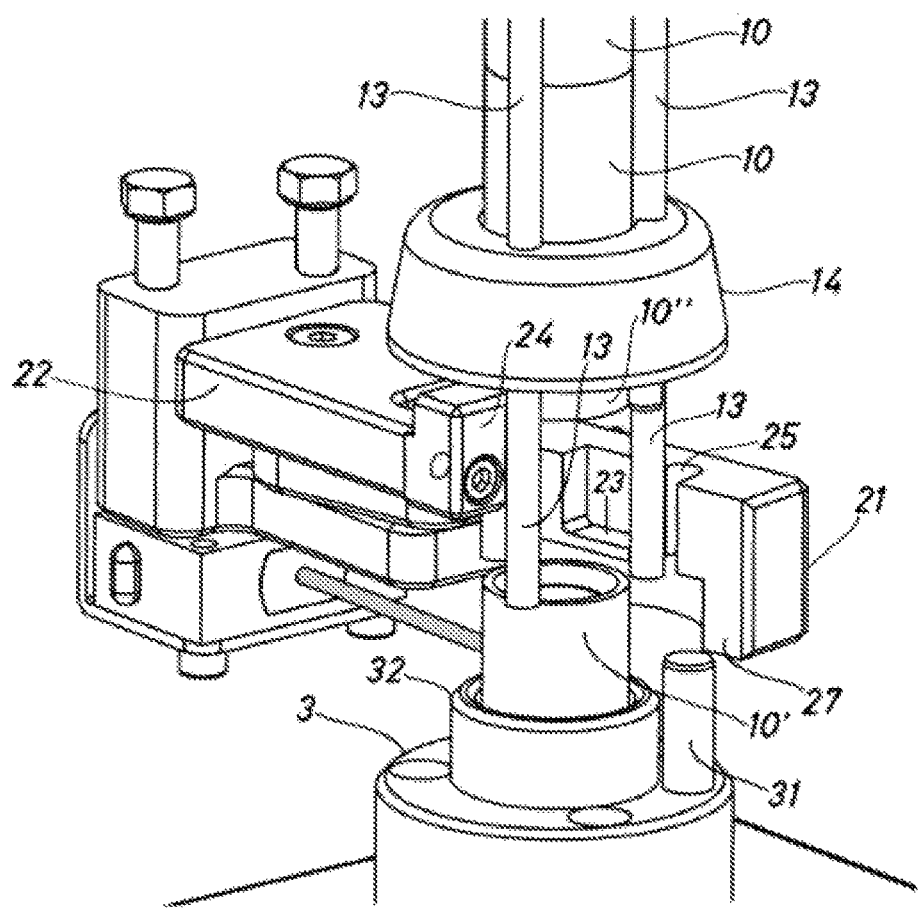
FIG. 3 is a perspective view of a detail of the lid-retaining mechanism of the device from FIG. 1.

The lids -10- stored in the holder -1- are dispensed by means of the retaining mechanism -2-, shown in the release position in FIG. 3 for reasons of clarity. The retaining mechanism -2- comprises a first arm -21- which comprises a rest -23-, a notch -25- and a contact region -27-. When the retaining mechanism -2- is in the predetermined retaining position (see FIGS. 1, 6, 9 and 10), the lids -10- in the holder -1- rest on top of the rest -23- of the first arm -21- and one of the columns -13- of the holder is housed in said notch -25-.

The retaining mechanism -2- also comprises a second arm -22- which has a projection -24-. In the release position (see FIGS. 3 and 8), a first lid -10'- is dispensed, said projection -24- of the retaining mechanism -2- being in contact with the following lid -10"- (see FIG. 8). The release position is achieved by causing a rotation on the first arm -21- by means of a rod -31- of the lid positioner -3-, said rod -31- contacting the contact region -27- of the first arm -21-, as shown in FIG. 3. The rod -31- is shown in a lower position in FIG. 3 such that the contact region -27- can be seen clearly. However, in order for the release position to be maintained, the rod -31- must be in contact with said contact region -27-. In the release position, a first lid -10'- to be dispensed falls onto a receiving region -32- of the positioner -3-.

Figure 4:
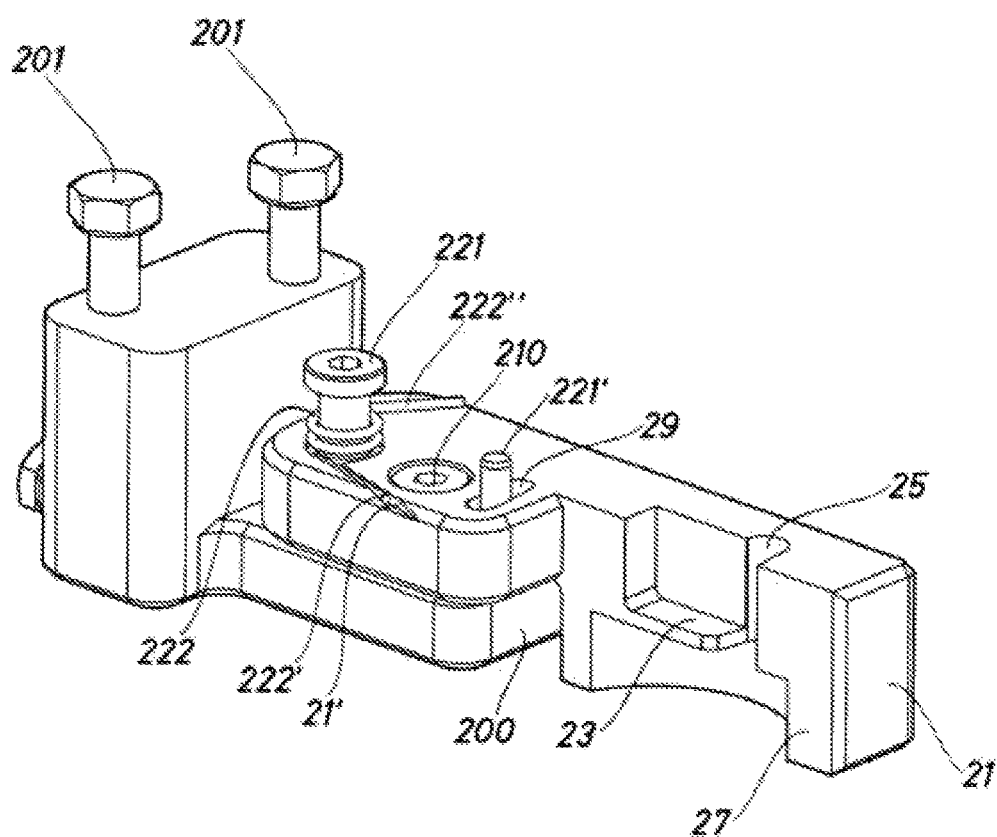
FIG. 4 is a perspective view of a detail of the lid-retaining mechanism of the device from FIG. 1, in which the second arm has been removed.
Figure 5:
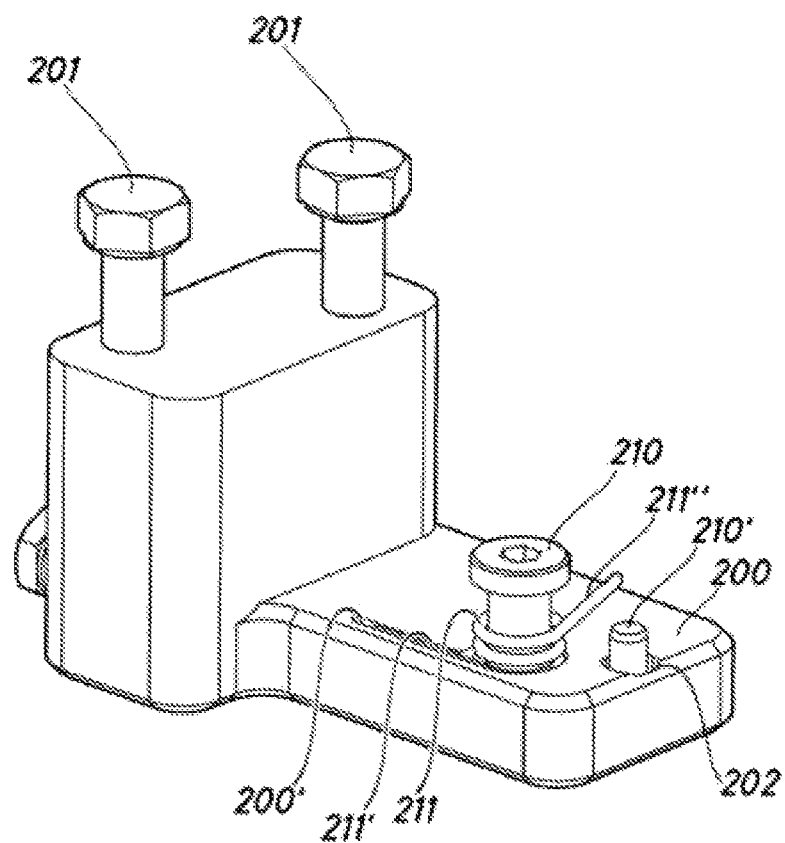
FIG. 5 is a perspective view of a detail of the lid-retaining mechanism of the device from FIG. 1, in which the first and the second arm have been removed.

The arms -21-, -22- of the retaining mechanism -2- are rotatably interconnected, as shown in FIGS. 4 and 5. The second arm -22- (not shown in FIGS. 4 and 5 for reasons of clarity) is rotatably attached to the first arm -21- by means of the bolt -221-, a torsion spring -222- comprising an end -222'- that is in contact with the first arm -21- and another end -222"- that is in contact with the second arm -22- being attached to said bolt -221-. The end -222"- that is in contact with the second arm -22- is introduced into a channel (not shown) of the second arm -22- in the same way as the end -222'- is in contact with the first arm -21- via a channel -21'-.

Furthermore (see FIGS. 4 and 5), the first arm -21- is rotatably attached, by means of a bolt -210-, to a base -200- which is connected to a fixed platform (not shown for reasons of clarity) by means of bolts -201-. Said fixed platform (not shown for reasons of clarity) is the same fixed platform to which the base -14- supporting the columns -13- of the holder -1- is attached. The bolt -210- which attaches the first arm -21- to the base -200- comprises a torsion spring -211- that has an end -211'- that is in contact with the base -200- and another end -211"- that is in contact with the first arm -21-. The end -211"- that is in contact with the first arm -21- is introduced into a channel (not shown) of the first arm -21- in the same way as the end -211'- that is in contact with the base -200- via a channel -200'-.

At the point when the rod -31- of the positioner -3- comes into contact with the contact region -27- of the first arm -21-, said first arm -21- rotates about the bolt -210- (see FIGS. 4 and 5) until a stop -210'- that is rigidly connected to the first arm -21- reaches the end of a slot -202- provided in the base -200-. As a result, the rotation of the first arm -21- is transmitted to the second arm -22- by means of the torsion spring -221-, the second arm -22- thus rotating about the bolt -221-. The second arm -22- comprises a stop -221'- that is rigidly connected thereto and that extends through a slot -29- in the first arm -21-, said slot -29- limiting the movement of the second arm -22- with respect to the first arm -21-.

Figure 8:
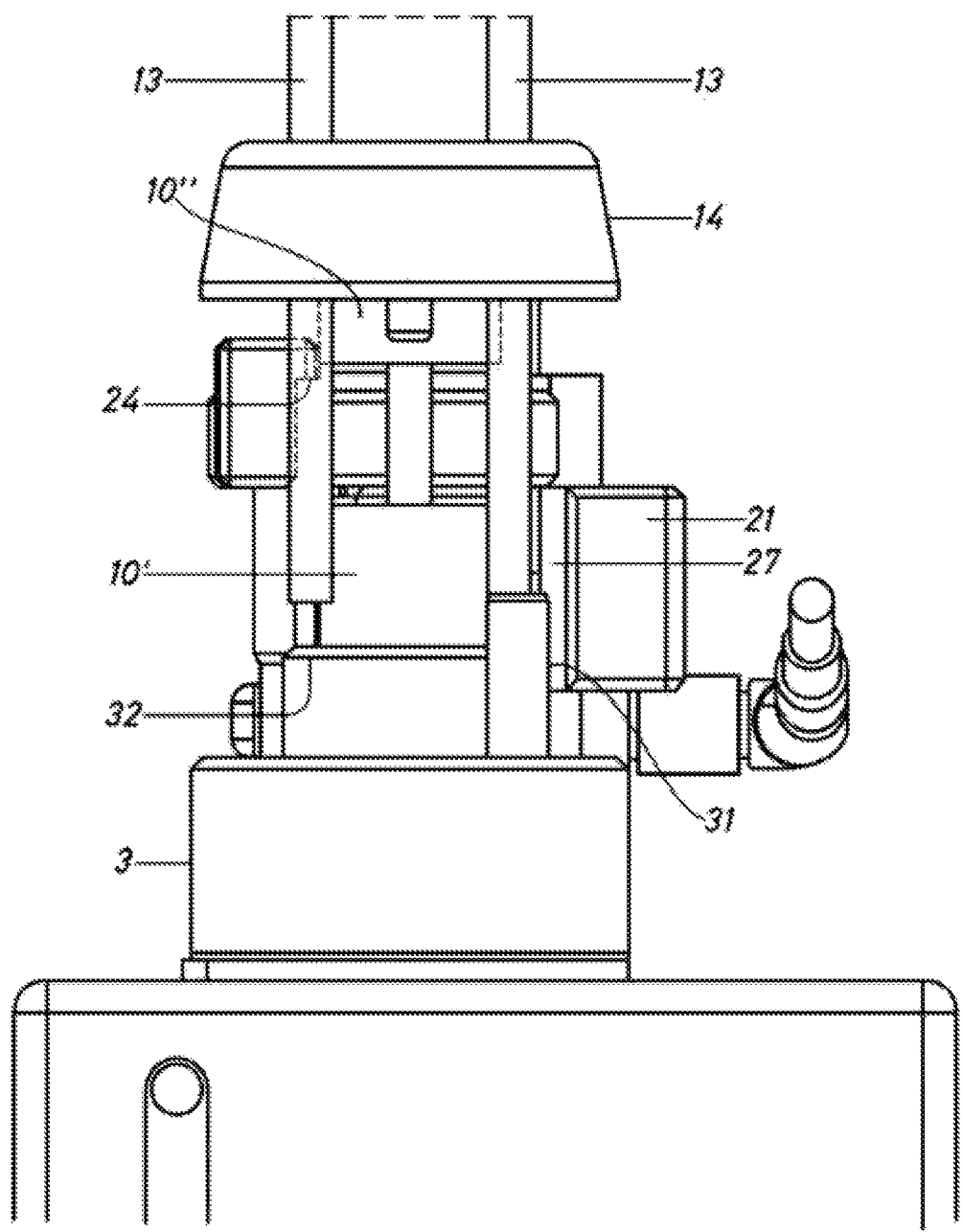
Figure 9:
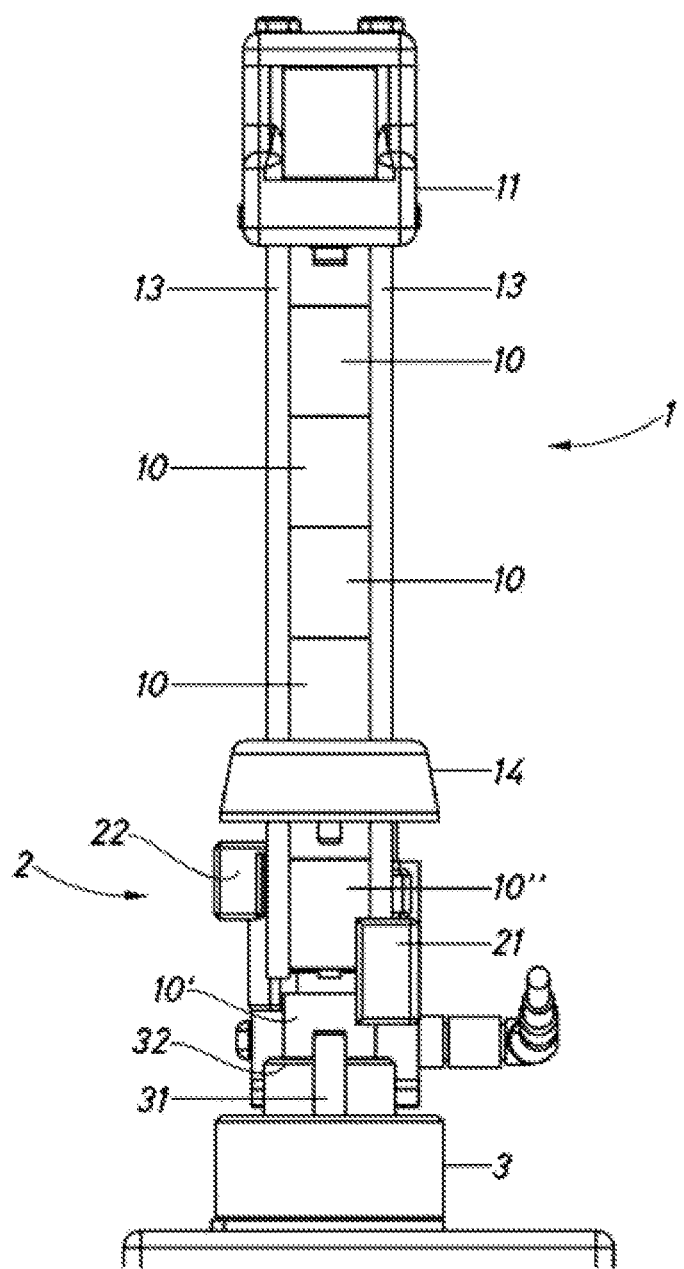
Figure 10:
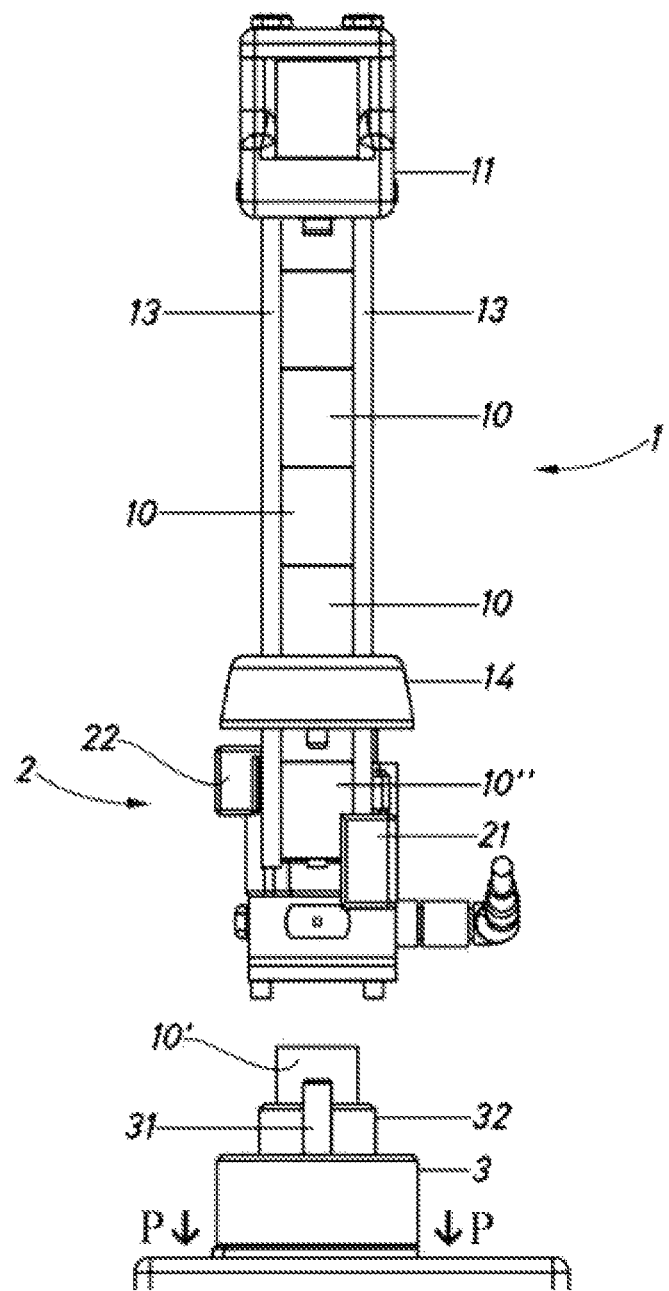

At the point when both arms -21-, -22- have reached the maximum rotation extent permitted by the stops -221'-, 210'- and their corresponding slots -29-, -202-, the retaining mechanism -2- is in the release position (see FIGS. 3 and 8).

The mechanism -2- returns to the predetermined retaining position (FIGS. 1, 6, 9 and 10) as the rod -31- of the positioner -3- stops applying pressure to the contact region -27- of the first arm -21-. In this situation, the torsion springs -222-, -211- return both arms -21-, -22- to their rest position (predetermined retaining position), causing them to rotate until, again, the stops -221'-, -210'-reach the end of their corresponding slots -29-, -202-.

Figure 6:
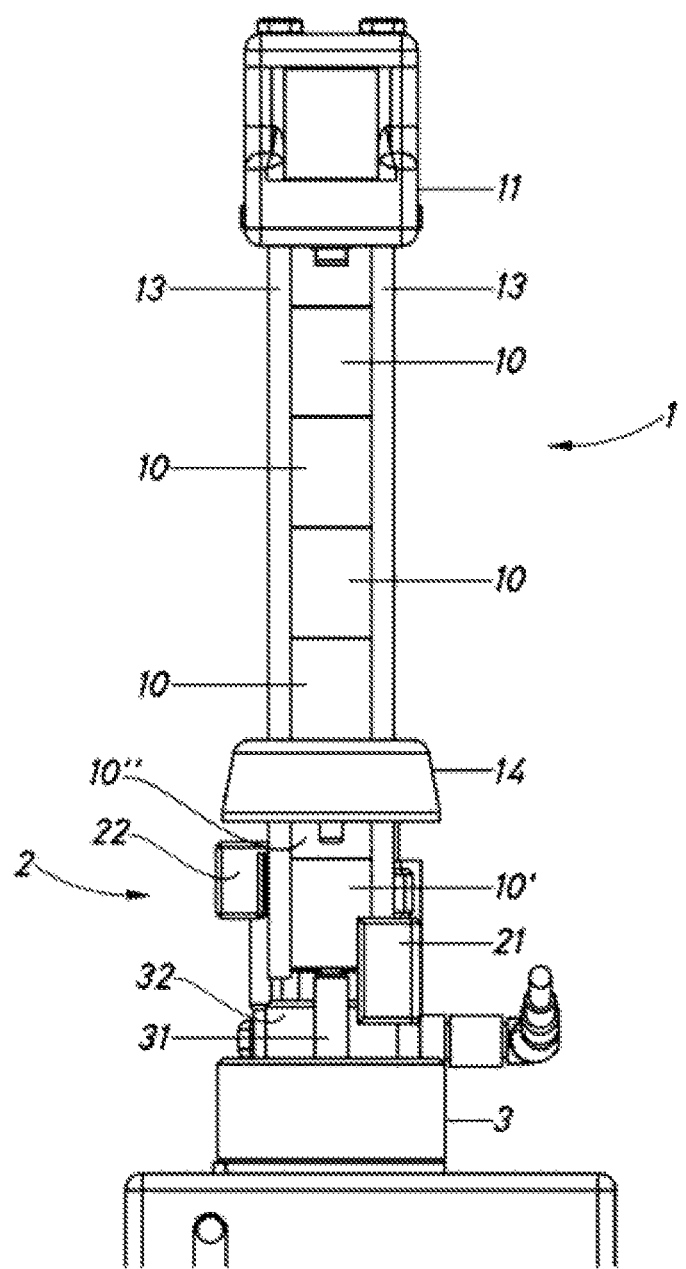
FIGS. 6 to 10 show a sequence of front views in which the device from FIG. 1 is shown during the process of dispensing a lid.

The only active component of the device is the positioner -3-, the function of which is, firstly, to dispense a first lid -10'- to be dispensed. As shown in FIG. 6, the positioner -3- is placed below the lid holder -1- at a height at which a rotation causes the rod -31- to touch the contact region -27- of the first arm -21-. To that effect, the positioner -3- rotates about an axis that is perpendicular to the surface of the face of the lids -10- to be dispensed and in the direction indicated by the arrow P (see FIG. 7).

Figure 7:
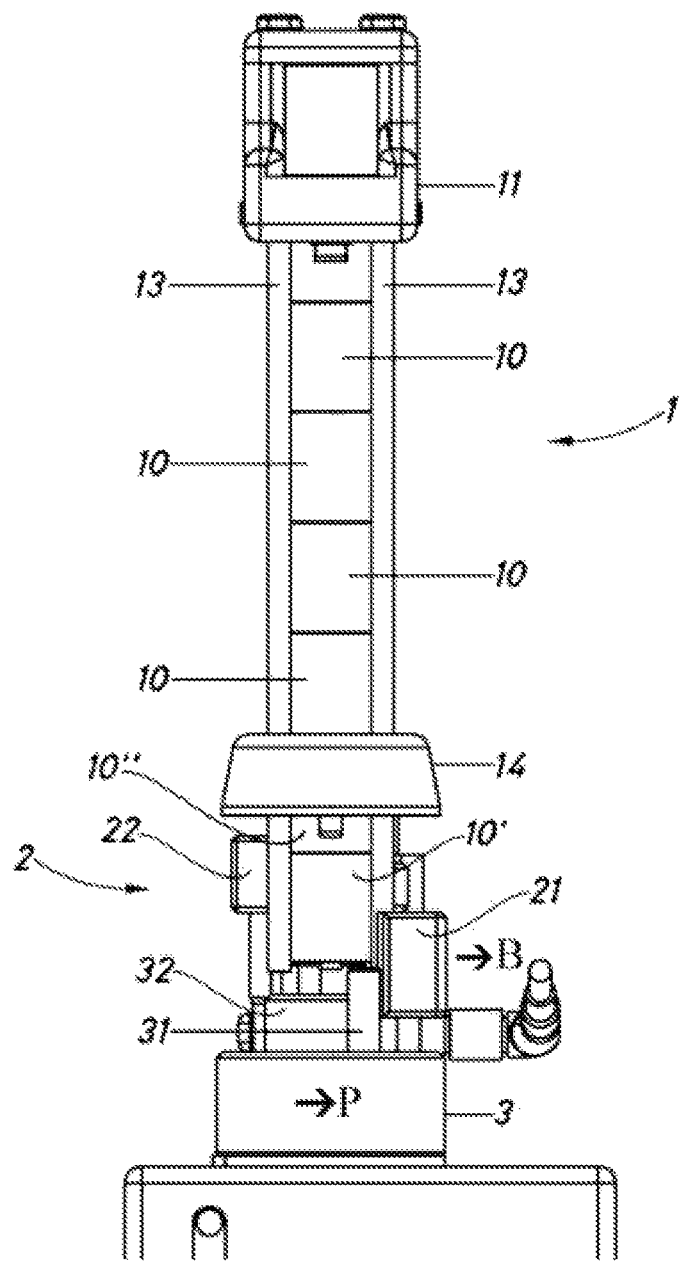

When the rod -31- comes into contact with the first arm -21- (see FIG. 6), said rod causes said first arm to rotate about the bolt -210- (see FIGS. 4 and 5) and to move in the direction of the arrow B (see FIG. 7). Rotation of the second arm -22- is also initiated in this manner, as explained above, until the release mechanism -2- is in the release position (see FIG. 8). In the release position, the rest -23- of the first arm -21- is at such a distance that the first lid -10'- to be dispensed cannot rest thereon. As a result, said first lid -10'- to be dispensed falls onto the receiving region -32- of the positioner -3-, and the following lid -10"- to be dispensed is kept retained by the projection -24- of the second arm -22- (see FIG. 8).

When the rod -31- of the positioner -3- stops acting on the first arm -21-, the retaining mechanism -2- returns to the predetermined retaining position thereof by virtue of the action of the torsion springs -222-, -211-. At this moment (see FIG. 9), the projection -24- of the second arm -22- stops supporting the following lid -10"- to be dispensed, causing said lid to fall onto the rest -23- of the first arm -21-. In this way, the retaining mechanism -2- is ready to dispense a new lid -10- when the positioner -3- acts on said mechanism once again.

Figure 11:
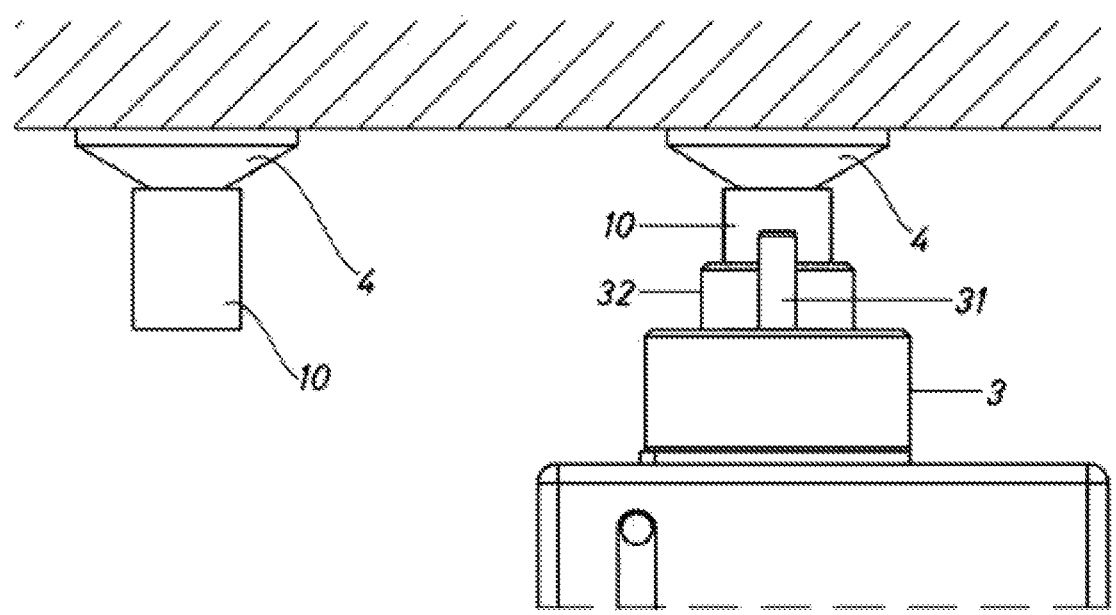
FIG. 11 is a front view in which the lid positioner of the device from FIG. 1 is shown placing a lid on a syringe.

Once a lid -10- has been dispensed, the positioner -3- moves away from the retaining mechanism -2- (see arrows Pin FIG. 10) and is placed below a syringe -4- in order to carry out placement of the lid -10- (see FIG. 11). The positioner -3- places the lid -10- by means of screwing, rotating about the same axis on which it rotates in order to dispense lids -10-.

Although the invention has been set out and described with reference to embodiments thereof, it should be understood that these do not limit the invention, and that it is possible to alter many structural or other details that may prove obvious to persons skilled in the art after interpreting the subject matter disclosed in the present description, claims and drawings. Therefore, the scope of the present invention includes any variant or equivalent that could be considered covered by the broadest scope of the following claims.

What is claimed is:

1. A device for placing threaded lids on containers, said device comprising:
   a receptacle configured to hold lids, said receptacle comprising an exit through which the lids stored in said receptacle are dispensed,
   a retainer configured to retain the lids stored in said receptacle, said retainer being arranged at the exit of said receptacle, said retainer having a predetermined retaining position in which the lids stored in said receptacle are retained, and a release position in which one of the lids stored in said receptacle is dispensed, and
   a positioner which is designed to move between a receiving position and a placing position, said positioner being able to rotate about a first axis, said positioner placing a threaded lid on a container by a first rotational movement of the positioner about said first axis when said positioner is in said placing position,
   wherein said positioner, when in said receiving position, causes the retainer to change from the predetermined retaining position to the release position by a second rotational movement of the positioner about said first axis,
   wherein the retainer comprises a first arm and a second arm for supporting the lids to be dispensed, the first arm and the second arm being rotatably interconnected, and
   wherein the second arm of the retainer comprises a projection which comes into contact with a second lid to be dispensed when the retainer is in the release position.

2. The device according to claim 1, wherein the retainer can rotate about a second axis parallel to said first axis, said retainer changing from the predetermined retaining position to the release position by a rotational movement of the retainer about said second axis.

3. The device according to claim 1, wherein the retainer comprises resilient means for returning to the predetermined retaining position, starting from the release position.

4. The device according to claim 1, wherein the first arm of the retainer comprises a rest on which a first lid to be dispensed rests when the retainer is in the predetermined retaining position.

5. The device according to claim 1, wherein the positioner comprises a region for receiving a threaded lid.

6. The device according to claim 1, wherein said receptacle comprises an entrance for manually supplying the threaded lids thereto.

7. The device according to claim 6, wherein said entrance for manually supplying the threaded lids is sized so as to match the dimensions of the threaded lids, said entrance having a raised surface supported by a spring, in order to prevent the threaded lids from being placed in an incorrect orientation.

8. A device for placing threaded lids on containers, said device comprising:
   a receptacle configured to hold lids, said receptacle comprising an exit through which the lids stored in said receptacle are dispensed,
   a retainer configured to retain the lids stored in said receptacle, said retainer being arranged at the exit of said receptacle, said retainer having a predetermined retaining position in which the lids stored in said receptacle are retained, and a release position in which one of the lids stored in said receptacle is dispensed, and
   a positioner which is designed to move between a receiving position and a placing position, said positioner being able to rotate about a first axis, said positioner placing a threaded lid on a container by a first rotational movement of the positioner about said first axis when said positioner is in said placing position,
   wherein said positioner, when in said receiving position, causes the retainer to change from the predetermined retaining position to the release position by a second rotational movement of the positioner about said first axis,
   wherein the retainer comprises a first arm and a second arm for supporting the lids to be dispensed, the first arm and the second arm being rotatably interconnected,
   wherein the positioner comprises a rod that is eccentric with respect to said first axis, such that the first rotational movement of the positioner about said first axis defines a trajectory of said rod, and
   wherein the first arm of the retainer intercepts said trajectory of said rod of the positioner such that, when the positioner carries out said second rotational movement about said first axis, said rod comes into contact with said first arm, causing said retainer to rotate from the predetermined retaining position to the release position.

9. The device according to claim 8, wherein the retainer can rotate about a second axis parallel to said first axis, said retainer changing from the predetermined retaining position to the release position by a rotational movement of the retainer about said second axis.

10. The device according to claim 8, wherein the retainer comprises resilient means for returning to the predetermined retaining position, starting from the release position.

11. The device according to claim 8, wherein the first arm of the retainer comprises a rest on which a first lid to be dispensed rests when the retainer is in the predetermined retaining position.

12. The device according to claim 8, wherein the positioner comprises a region for receiving a threaded lid.

13. The device according to claim 8, wherein said receptacle comprises an entrance for manually supplying the threaded lids thereto.

14. The device according to claim 13, wherein said entrance for manually supplying the threaded lids is sized so as to match the dimensions of the threaded lids, said entrance having a raised surface supported by a spring, in order to prevent the threaded lids from being placed in an incorrect orientation.

\* \* \* \* \*